United States Patent [19]
Rise

[11] Patent Number: 5,782,798
[45] Date of Patent: Jul. 21, 1998

[54] TECHNIQUES FOR TREATING EATING DISORDERS BY BRAIN STIMULATION AND DRUG INFUSION

[75] Inventor: Mark T. Rise, Monticello, Minn.

[73] Assignee: Medtronic, Inc., Minneapolis, Minn.

[21] Appl. No.: 674,498

[22] Filed: Jun. 26, 1996

[51] Int. Cl.$^6$ .................................................. A61M 31/00
[52] U.S. Cl. ............................... 604/49; 607/45; 607/72; 604/93; 604/890.1
[58] Field of Search ........................... 604/19, 48, 49, 604/50, 51, 93, 890.1, 891.1; 607/45, 72; 128/898

[56] References Cited

U.S. PATENT DOCUMENTS

| | | | |
|---|---|---|---|
| 4,646,744 | 3/1987 | Capel | 607/58 |
| 5,263,480 | 11/1993 | Wernicke et al. | 607/118 |
| 5,458,631 | 10/1995 | Xavier | 604/891.1 |
| 5,487,739 | 1/1996 | Aebisher et al. | 604/890.1 |
| 5,540,734 | 7/1996 | Zabara | 607/45 |

OTHER PUBLICATIONS

Bartley G. Hoebel, *Pharmacologic Control of Feeding*, Ann. Rev. Pharmacol. Toxicol., vol. 17, 1977, pp. 605–621.

Bartley G. Hoebel and Sarah F. Leibowitz, *Brain Monoamines in the Modulation of Self-Stimulation, Feeding, and Body Weight*, Brain, Behavior and Bodily Disease, Raven Press, New York, 1981, pp. 103–142.

Brown et al., *Changes in Food Intake with Electrical Stimulation of the Ventromedial Hypothalamus in Dogs*, J. Neurosurg., vol. 60, Jun., 1984, pp. 1253–1257.

Sarah F. Leibowitz, *Brain Monoamines and Peptides: Role in the Control of Eating Behavior*, Federation Proceedings, vol. 45, No. 5, Apr. 1986, pp. 1396–1403.

Campfield et al., *Recombinant Mouse OB Protein: Evidence for a Peripheral Signal Linking Adiposity and Central Neural Networks*, Science, vol. 269, Jul. 28, 1995, pp. 546–549.

Shiosaki et al., *Boc–CCK–4 Derivatives Containing Side–Chain Ureas as Potent and Selective CCK–A Receptor Agonists*, Journal of Medicinal Chemistry, vol. 34, No. 9, 1991, pp. 2837–2842.

B. Glenn Stanley, *Neuropeptide Y in Multiple Hypothalamic Sites Controls Eating Behavior, Endocrine, and Autonomic Systems for Body Energy Balance*, The Biology of Neuropeptide Y and Related Peptides, Humana Press Inc., Totowa, NJ, 1993, pp. 457–509.

Vettor et al., *Induction and Reversibility of an Obesity Syndrome by Intracerebroventricular Neuropeptide Y Administration to Normal Rats*, Diabetologia, vol. 37, 1994, pp. 1202–1208.

Pelleymounter et al., *Effects of the Obese Gene Product on Body Wieght Regulation in ob/ob Mice*, Science, vol. 269, Jul. 28, 1995, pp. 540–542.

Halaas et al., *Weight–Reducing Effects of the Plasma Protein Encoded by the Obese Gene*, Science, vol. 269, Jul. 28, 1995, pp. 543–546.

Stephens et al., *The Role of Neuropeptide Y in the Antiobesity Action of the Obese Gene Product*, Nature, vol. 377, Oct. 12, 1995, pp. 530–532.

Turton et al., *A Role of Glucagon–Like Peptide–1 in the Central Regulation of Feeding*, Nature, vol. 379, Jan. 4, 1996, pp. 69–72.

Spedding et al., *Neural Control of Dieting*, Nature, vol. 380, Apr. 11, 1996, p. 488.

(List continued on next page.)

*Primary Examiner*—Mark Bockelman
*Assistant Examiner*—Jennifer R. Sadula
*Attorney, Agent, or Firm*—Banner & Witcoff, Ltd

[57] ABSTRACT

Techniques using one or more drugs and/or electrical stimulation for treating an eating disorder by means of an implantable signal generator and electrode and/or an implantable pump and catheter. A catheter is surgically implanted in the brain to infuse the drugs, and one or more electrodes may be surgically implanted in the brain to provide electrical stimulation.

48 Claims, 3 Drawing Sheets

OTHER PUBLICATIONS

Miller et al., *JAK/STAT Eats the Fat, TINS*, vol. 19, No. 5, 1996, pp. 159–161.

Sarah F. Leibowitz and B. Glenn Stanley, *Brain Peptides and the Control of Eating Behavior, Neural and Endocrine Peptides and Receptors*, Plenum Press, New York and London, Spring Symposium Series, pp. 333–352.

TECHNIQUES FOR TREATING EATING DISORDERS BY BRAIN STIMULATION AND DRUG INFUSION

BACKGROUND OF THE INVENTION

1. Field of the Invention

This invention relates to nerve tissue stimulation and infusion techniques, and more particularly relates to such techniques for treating eating disorders.

2. Description of the Related Art

Some people suffer from chronic eating disorders, including anorexia and morbid obesity. The neural circuitry of the brain that controls eating and satiety include neurons in the lateral hypothalamus (feeding) and the ventral medial hypothalamus (satiety).

Brown et al. have shown in dogs that stimulation of the ventral medial hypothalamic nucleus following 24 hours of food deprivation delayed feeding behavior for up to 18 hours. Dogs stimulated for one hour every 12 hours for 3 days maintained an average daily food intake of 35% of normal baseline levels [*J Neurosurg* 60:1253–1257, 1984].

SUMMARY OF THE INVENTION

A preferred form of the invention uses one or more drugs and/or electrical stimulation to treat an eating disorder. The treatment is carried out by an implantable pump and a catheter having a proximal end coupled to the pump and having a discharge portion for infusing therapeutic dosages of the one or more drugs into a predetermined infusion site in brain tissue. The treatment also may be carried out by an implantable signal generator and an implantable electrode having a proximal end coupled to the signal generator and having a stimulation portion for electrically stimulating a predetermined stimulation site in the brain tissue. According to one embodiment of the invention, the stimulation and infusion can be carried out in the lateral hypothalamus, the paraventricular nucleus and the ventral medial hypothalamus, thereby treating the eating disorder. By using the foregoing techniques, the symptoms of eating disorders, such as anorexia and morbid obesity, can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
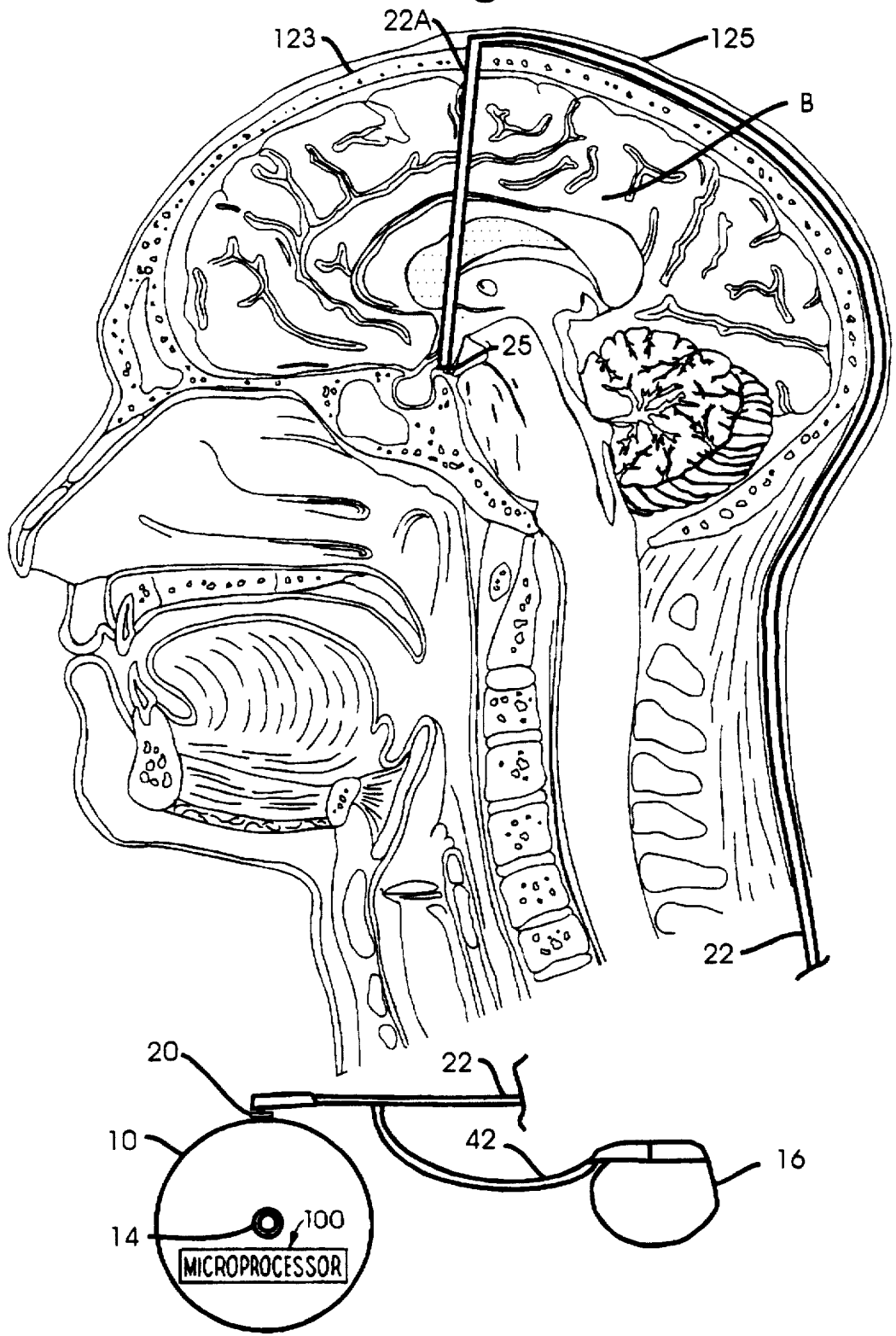
FIG. 1 is a diagrammatic illustration of a combined catheter and electrode implanted in a brain according to a preferred embodiment of the present invention, and a signal generator and pump coupled to the combined catheter and electrode.

Referring to FIG. 1, a system or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan) ("the '147 Patent"), assigned to Medtronic, Inc., Minneapolis, Minn., which is incorporated by reference.

The distal end of catheter 22 terminates in a cylindrical hollow tube 22A having a distal end 25 implanted into the brain parenchyma of the satiety or feeding centers to induce the behavior that is desired by conventional stereotactic surgical techniques. Alternatively, tube 22A can be installed into the cerebral ventricles. End 25 is provided with microporous portions 27–29 (FIG. 3) in the preferred embodiment; however, multiple holes or slits within portions 27–29 also could be used. Additional details about portions 27–29 may be obtained from pending U.S. application Ser. No. 08/430,960 entitled "Intraparenchymal Infusion Catheter System," filed Apr. 28, 1995 in the name of Dennis Elsberry et al. and assigned to the same assignee as the present application.

Figure 2:
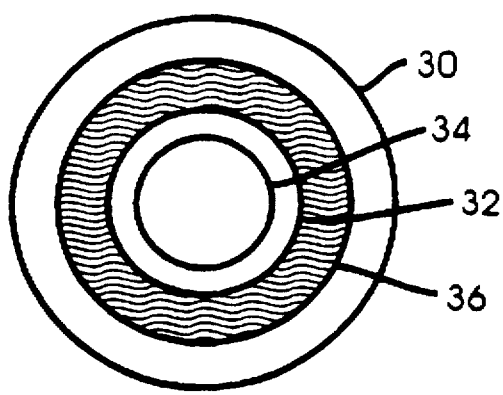
FIG. 2 is a cross-sectional view of the catheter-electrode taken along line 2—2 of FIG. 3.

Referring to FIG. 2, tube 22A includes an outer cylindrical insulating jacket 30 and an inner cylindrical insulating jacket 32 that defines a cylindrical catheter lumen 34. A multifilar coil of wire, multifilar stranded wire or flexible printed circuit 36 is embedded in tube 22A as shown.

Tube 22A is surgically implanted through a hole in the skull 123 and catheter 22 is implanted between the skull and the scalp 125 as shown in FIG. 1. A stylet may be placed into the center of tube 22A to give it stiffness when introducing the tube into the brain. After the stylet is removed, center lumen 34 constitutes a catheter which can be used to infuse an agent, including a drug. Catheter 22 is joined to implanted device 10 in the manner shown.

Catheter 22 may be divided into twin tubes, tube 22A and a second tube 22B (not shown), that are implanted into the brain bilaterally. Alternatively, the second tube may be supplied with drugs from a separate catheter and pump and with electrodes from a separate signal generator.

Referring again to FIG. 1, a system or device 16 made in accordance with the preferred embodiment also may be implanted below the skin of a patient. Device 16 may take the form of a signal generator Model 7424 manufactured by Medtronic, Inc. under the trademark Itrel II.

Figure 3:
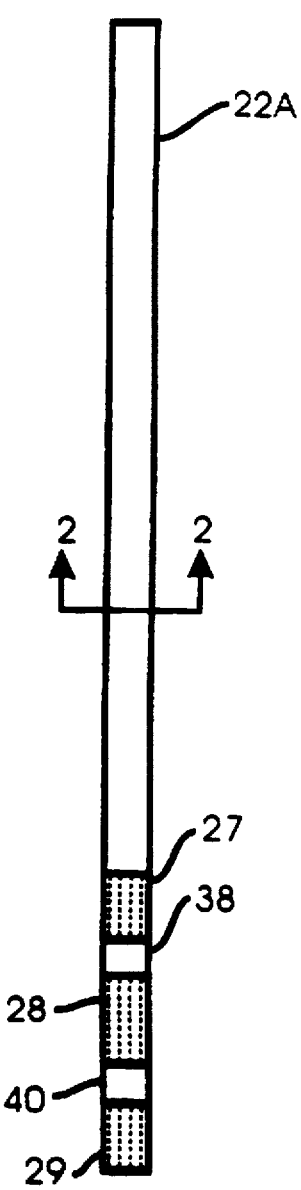
FIG. 3 is a diagrammatic view of the catheter-electrode shown in FIG. 1.

The distal end of tube 22A terminates in stimulation electrodes 38 and 40 (FIG. 3). While the preferred embodiment shows two electrodes on tube 22A, some applications may required a greater or lesser number. When one electrode is used, a portion of the case of device 16 may serve as a reference electrode. Each of electrodes 38 and 40 is individually connected to device 16 through a conductor in wire 36 (FIG. 2). The wires exit catheter 22 to form a cable 42 which is joined to implanted device 16 in the manner shown in FIG. 1. Device 16 is implanted in a human body, preferably in the chest cavity or in the abdomen.

The preferred embodiment consists of a single tube 22A on which are intermingled electrodes 38 and 40 between microporous portions 27–29. An alternative embodiment would be to have electrodes 38 and 40 located on a second tube 22C (not shown) inserted into the brain parenchyma in another location.

The present invention may be implemented by providing seven different drug dosages from 0 dosage to a 1.0 ml dosage with 0.1 ml increments between choices. The time interval between dosages can be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 11B) of the '147 Patent. The selected dosage and interval of a drug is then delivered through catheter 22 and tube 22A to the portions of the brain identified in Table I in the manner described in the '147 Patent.

The appropriate drugs for use in connection with the lateral hypothalamus, paraventricular nucleus or the ventral medial hypothalamus of brain B (FIG. 1) in which tube 22A terminates, together with the effect of the drug on that portion of the brain for treatment of various eating disorders are provided in the following Table I:

TABLE I

| ACTION | INFUSION TYPE | BRAIN LOCATION |
|---|---|---|
| OBESITY TREATMENT | | |
| Increase Satiety | Norepinephrine Antagonist | Paraventricular Nucleus |
| | Opiate Antagonist | Paraventricular Nucleus |
| | Pancreatic Polypeptide Blocker | Paraventricular Nucleus |
| | GABA Agonist | Paraventricular Nucleus |
| | Serotonin Agonist | Ventral Medial Hypothalamus |
| | Calcitonin Agonist | Paraventricular Nucleus |
| | Corticotropin-releasing factor Agonist | Paraventricular Nucleus |
| | Neurotensin Agonist | Paraventricular Nucleus |
| Decrease Hunger | Dopamine Agonist | Lateral Hypothalamus |
| | Pancreatic Polypeptide Blocker | Lateral Hypothalamus |
| | Norepinephrine Agonist | Lateral Hypothalamus |
| | Anesthetic | Lateral Hypothalamus |
| | Glucagon Agonist | Lateral Hypothalamus |
| ANOREXIA TREATMENT | | |
| Reduce Satiety | Norepinephrine Agonist | Paraventricular Nucleus |
| | Opiate Agonist | Paraventricular Nucleus |
| | Pancreatic Polypeptide Agonist | Paraventricular Nucleus |
| | GABA Agonist | Paraventricular Nucleus |
| | Calcitonin Antagonist | Paraventricular Nucleus |
| | Corticotropin-releasing factor Antagonist | Paraventricular Nucleus |
| | Serotonin Antagonist | Ventral Medial Hypothalamus |
| | Anesthetic | Ventral Medial Hypothalamus |
| Increase Hunger | Dopamine Antagonist | Lateral Hypothalamus |
| | Norepinephrine Antagonist | Lateral Hypothalamus |
| | Pancreatic Polypeptide Agonist | Lateral Hypothalamus |
| | Glucagon Antagonist | Lateral Hypothalamus |

Table I lists agents that act as agonists or antagonists to the transmitters acting in a particular place in the brain. Agents that block the reuptake or enzymatic breakdown of those transmitters or cause them to be released from their synaptic vesicles could be substituted for agonists. Enzymes that would speed up the breakdown of transmitters could be used as an alternative to antagonists. Agents, such as Bombesin, which have a generalized effect may be infused into the ventricles or hypothalamus.

Typical stereotactic coordinates for portions of a normal brain described in Table I are identified in Table II:

TABLE II

| BRAIN LOCATIONS | ANTERIOR POSTERIOR | DORSAL VENTRAL | MEDIAL LATERAL |
|---|---|---|---|
| Lateral Hypothalamus | 0.2 to 1.4 | −0.1 to −1.5 | 0.5 to 1.0 |
| Paraventricular Hypothalamus | 0.8 to 1.2 | −0.1 to −0.5 | 0.05 to 0.4 |
| Ventral Medial Hypothalamus | 0.6 to 1.2 | −0.6 to −1.5 | 0.1 to 0.5 |

In the foregoing table: the medi-lateral dimensions are relative to the midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to said line; all dimensions are in centimeters. The lateral hypothalamus includes the parafornical hypothalamus.

Delivery of the drugs to the specific target locations described above will result in the fewest neurological side effects since the effects of the drugs on other neurons subserving other functions is minimized. However, it is still possible to achieve an acceptable, if not optimal, therapeutic-effects-to-side-effects ratio by delivering agents to the ventricular space or subdurally. In particular, agents may be efficiently delivered to the third ventricle.

Exemplary drugs with their ranges of dosages and drug concentrations for some of the classes of drugs identified in Table I are provided in the following Table III. Some of the classes of drugs will require further pharmaceutical development.

TABLE III

| DRUG CLASS | SPECIFIC DRUG | DOSING RANGE |
|---|---|---|
| Adrenergic Agonist | Clonidine HCL | 10 nM–50 muM |
| | Ephedrine HCL | 10 nM–50 muM |
| | Norepinephrine | 10 nM–50 muM |
| Adrenergic Antagonists | Verapamil HCL | 10 nM–50 muM |
| | Propranolol | 10 nM–50 muM |
| | Urapidil HCL | 10 nM–50 muM |
| Opioid Agonist | Morphine | 0.1–500 muM |
| Opioid Antagonist | Naloxone | 0.1–500 muM |
| Serotonin Agonist | Buspirone HCL | 10 nM–50 muM |
| | L-methyl serotonin | 10 nM–50 muM |
| Serotonin Antagonist | (−) Sulpiride | 0.05–1 muM |
| | spiperone HCL | 0.1–10 muM |
| | Propranolol HCL | 0.05–1 muM |
| Pancreatic Polypeptide Agonist | NPY | 20–300 picoM |
| | PYY | 2 picoM to 10 muM |
| Pancreatic Polypeptide Antagonist | Leptin | 2 picoM to 10 muM |
| GABA Agonists | baclofen | 0.1–10 muM |
| | muscinol HBr | 100–500 muM |
| GABA Antagonists | Gabazine | 1–50 muM |
| | Saclofen | 0.5–25 muM |
| | Bicuulline | 1–100 muM |
| | picrotoxin | 10–100 muM |
| Dopamine Antagonist | (+) apomorphone HCL | 5–20 muM |
| | spiperone HCL | 0.1–10 muM |
| | haloperidol | 10–100 muM |
| | (−) Sulpiride | 0.05–1 muM |
| Dopamine Agonist | methanesulfonate | 1–10 muM |
| Dopamine Agonist (cont.) | (−) apomorphine pergolide | 10–30 muM |
| Glucagon Agonist | GLP-1 | 0.05–500 muM |
| Glucagon Antagonist | exendin (9-39) | 0.01–500 muM |
| Anesthetic | Lidocaine hydrochloride | 5–20 muM |

In the preceding table, muM means micromolar, nM means nanomolar and picoM means picomolar.

Microprocessor 100 within device 10 can be programmed so that a controlled amount of drug described in Table III can be delivered to the specific brain sites described in Tables I and II.

The applicant has discovered that eating disorders, including anorexia and morbid obesity, can be treated by electrically stimulating brain tissue either alone or while drugs are being administered as described above. The stimulation can be achieved by an ITREL II signal generator implemented as device 16 (FIG. 1).

Electrical stimulation of nerve tissue may be implemented by providing pulses to electrodes 38 and 40 (FIG. 3) having amplitudes of 0.1 to 20 volts, pulse widths varying from 0.02 to 1.5 milliseconds, and repetition rates varying from 2 to 2500 Hz. The appropriate stimulation pulses are generated by device 16. The type of stimulation administered by device 16 to the brain depends on the specific location at which the electrodes 38 and 40 of tube 22A are surgically implanted.

The appropriate stimulation for use in connection with the lateral hypothalamus, paraventricular hypothalamus or ventral medial hypothalamus of the brain in which tube 22A terminates, together with the effect of the stimulation on that portion of the brain for an eating disorder is provided in the following Table IV:

TABLE IV

| ACTION | STIMULATION TYPE | BRAIN LOCATION |
| --- | --- | --- |
| OBESITY TREATMENT | | |
| Increase Satiety | Low Frequency | Ventral Medial Hypothalamus |
| | Low Frequency | Paraventricular Nucleus |
| Decrease Hunger | High Frequency | Lateral Hypothalamus |
| ANOREXIA TREATMENT | | |
| Reduce Satiety | High Frequency | Ventral Medial Hypothalamus |
| | High Frequency | Paraventricular Nucleus |
| Increase Hunger | Low Frequency | Lateral Hypothalamus |

In Table IV, low frequency means 100 Hz or less; high frequency means more than 100 Hz.

Coordinates for the portions of the brain described in Table IV are the same as those described in Table II above.

A microprocessor within device 16 can be programmed so that the desired stimulation can be delivered to the specific brain sites described in Table IV.

Figure 4A:
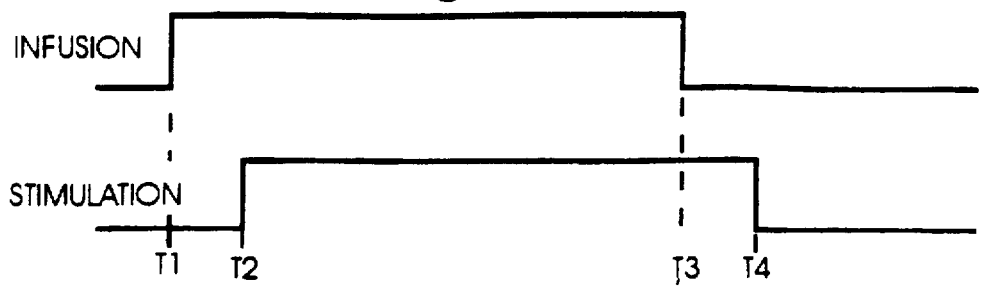
FIGS. 4A–4C are timing diagrams showing the relationship between the administration of drugs and electrical stimulation to nerve tissue.
Figure 4B:
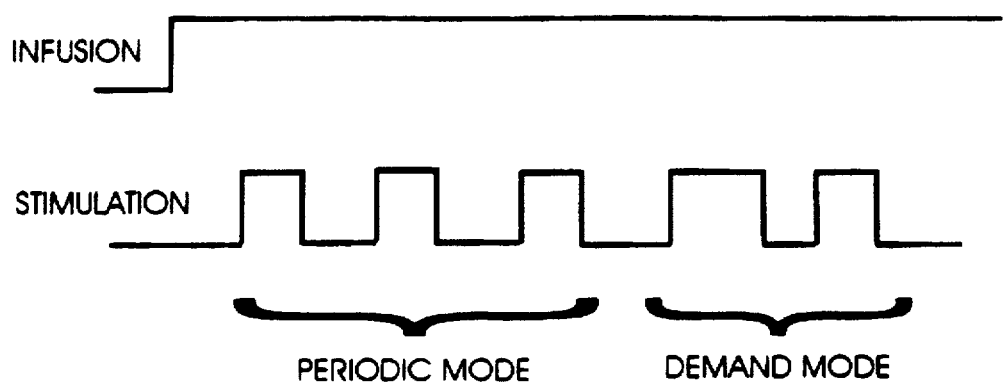
Figure 4C:
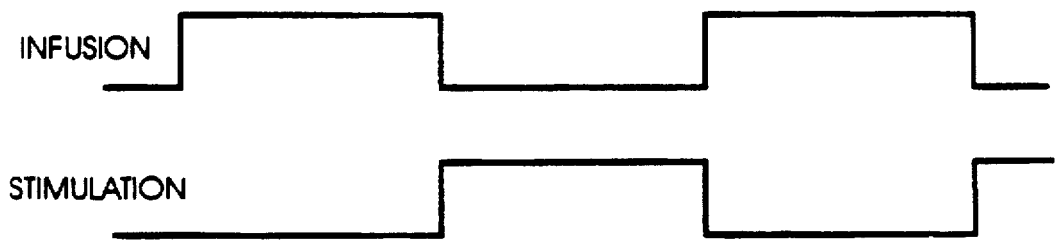

FIGS. 4A through 4C illustrate various times at which infusion and stimulation can be applied by tube 22A. For example, referring to FIG. 4A, infusion alone can be applied from time T1 to T2, infusion and stimulation can both be applied from time T2 to T3, and stimulation alone can be applied from time T3 to T4. This scenario might be used with electrode catheter configuration 22A (FIG. 3) to deliver a precursor of the transmitter substance used by the neurons being stimulated.

Alternatively, referring to FIG. 4B, stimulation might be applied intermittently to a background of continuous (FIG. 4B) or modulated (not shown) infusion. An example of how this might be used, considering the therapy for morbid obesity, is programming pump 10 to deliver a background infusion of drug to control appetite and programming stimulation device 16 to periodically apply stimulation to increase appetite suppression. The periods of stimulation might coincide with normal periods of the day when appetite increases, such as meal times. Alternatively, periods of stimulation may be triggered by a signal telemetered to the implanted device by the patient at times when the patient experiences increased hunger. The patient would use a small programmer, such as the one available with the ITREL II. This approach might be used in combination with the combined electrode/catheter (tube 22A) shown in FIG. 3 or when using electrodes and catheters placed on separate tubes. When treating anorexia, the patient might activate hunger inducing or satiety reducing stimulus or infusion in order to eat meals specified by a prescribed diet. FIG. 4B depicts a periodic stimulation on a background of infusion; however, infusion over a background of stimulation is also possible.

Still another approach would be to follow the regimen depicted in FIG. 4C. By alternating the application of stimulation and infusion, a continuous control of appetite is achieved by activating different populations of neurons for less than continuous periods of time. This method advantageously may reduce the risk of damaging one population of neurons through overactivation. While FIG. 4C depicts altering stimulation and infusion, it could also apply to a scheme of altering stimulation or infusions delivered to multiple sites.

Combinations of stimulation and infusion at multiple sites could be used to control different aspects of hunger and satiety. Infusion or stimulation at one site may selectively control hunger for fat while stimulation or infusion at another site could be used to control hunger for carbohydrates. In this case, the infusion and stimulation timing diagrams (not shown) may be quite elaborate with varying degrees of synchronization.

By using the foregoing techniques for simultaneous drug infusion and electrical stimulation, eating disorders can be controlled with a degree of accuracy previously unattainable. Those skilled in that art will recognize that the preferred embodiments may be altered or amended without departing from the true spirit and scope of the invention, as defined in the accompanying claims.

I claim:

1. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the at least one electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion of the at least one drug into the infusion site.

2. A method, as claimed in claim 1, wherein the stimulation site and the infusion site are each a respective one of a paraventricular nucleus, a lateral hypothalamus, and a ventral medial hypothalamus of the brain of the patient.

3. A method, as claimed in claim 2, wherein the signal generator generates pulses having a repetition rate of less than 100 Hz and wherein the step of surgically implanting the at least one electrode comprises a step of implanting the stimulation portion in the lateral hypothalamus, wherein electrical stimulation of the lateral hypothalamus with the pulses causes the patient to eat.

4. A method, as claimed in claim 2, wherein the signal generator generates pulses having a repetition rate of less than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes an increase in satiety for the patient.

5. A method, as claimed in claim 2, wherein the signal generator generates pulses having a repetition rate of greater than 100 Hz and wherein the step of surgically implanting the at least one electrode comprises a step of implanting the stimulation portion in the lateral hypothalamus, wherein electrical stimulation of the lateral hypothalamus with the pulses causes a reduction in appetite for the patient.

6. A method, as claimed in claim 2, wherein the signal generator generates pulses having a repetition rate of greater than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes a reduction in satiety for the patient.

7. A method, as claimed in claim 1, wherein the at least one drug is one of an antagonist and a blocker substance and wherein the step of surgically implanting the catheter comprises a step of surgically implanting the discharge portion in a paraventricular nucleus of the brain of the patient, wherein drug infusion of the at least one drug into the paraventricular nucleus causes an increase in satiety for the patient.

8. A method, as claimed in claim 1, wherein the at least one drug is an agonist and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes an increase in satiety for the patient.

9. A method, as claimed in claim 1, wherein the at least one drug is one of an agonist, a blocking substance, and an anesthetic and wherein the step of surgically implanting the catheter comprises a step of surgically implanting the discharge portion in a lateral hypothalamus of the brain of the patient, wherein drug infusion of the at least one drug into the lateral hypothalamus causes a decrease in hunger for the patient.

10. A method, as claimed in claim 1, wherein the at least one drug is one of an agonist, an antagonist, and an anesthetic and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes a reduction in satiety for the patient.

11. A method, as claimed in claim 1, wherein the at least one drug is one of an agonist and an antagonist and wherein the step of surgically implanting the catheter comprises a step of surgically implanting the discharge portion in a lateral hypothalamus of the brain of the patient, wherein drug infusion of the at least one drug into the lateral hypothalamus causes an increase in hunger for the patient.

12. A method for therapeutically treating an eating disorder of a patient having a central nervous system including a brain and a spinal cord, the method comprising the steps of:

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient; and operating the pump to discharge a predetermined dosage of at least one drug through the discharge portion of the catheter into the predetermined infusion site, whereby an eating disorder of the patient is treated by drug infusion of the at least one drug into the infusion site on the central nervous system.

13. A method, as claimed in claim 12, wherein the at least one drug is one of an antagonist and a blocker substance and wherein the step of surgically implanting the catheter comprises a step of surgically implanting the discharge portion in a paraventricular nucleus of the brain of the patient, wherein drug infusion of the at least one drug into the paraventricular nucleus causes an increase in satiety for the patient.

14. A method, as claimed in claim 12, wherein the at least one drug is an agonist and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes an increase in satiety for the patient.

15. A method, as claimed in claim 12, wherein the at least one drug is one of an agonist, a blocking substance, and an anesthetic and wherein the step of surgically implanting the catheter comprises a step of surgically implanting the discharge portion in a lateral hypothalamus of the brain of the patient, wherein drug infusion of the at least one drug into the lateral hypothalamus causes a decrease in hunger for the patient.

16. A method, as claimed in claim 12, wherein the at least one drug is one of an agonist, an antagonist, and an anesthetic and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes a reduction in satiety for the patient.

17. A method, as claimed in claim 12, wherein the at least one drug is an agonist and an antagonist and wherein the step of surgically implanting the catheter comprises a step of surgically implanting the discharge portion in a lateral hypothalamus of the brain of the patient, wherein drug infusion of the at least one drug into the lateral hypothalamus causes an increase in hunger for the patient.

18. A method for therapeutically treating an eating disorder of a patient having a central nervous system including a brain and a spinal cord, the method comprising the steps of:

surgically implanting at least one electrode within the central nervous system, each electrode having a proximal end coupled to a signal generator and having a stimulation portion that is implanted at a predetermined stimulation site in the central nervous system of the patient, the predetermined stimulation site being a site on the central nervous system that controls at least one of hunger and satiety for the patient; and operating the signal generator to generate a signal to be applied on the at least one electrode to stimulate the stimulation site, whereby the eating disorder of the patient is treated by electrical stimulation of the predetermined stimulation site with the signal generated by the signal generator.

19. A method, as claimed in claim 18, wherein the stimulation site is one of a paraventricular nucleus, a lateral hypothalamus, and a ventral medial hypothalamus of the brain of the patient.

20. A method, as claimed in claim 19, wherein the signal generator generates pulses having a repetition rate of less than 100 Hz and wherein the step of surgically implanting the at least one electrode comprises a step of implanting the stimulation portion in the lateral hypothalamus, wherein electrical stimulation of the lateral hypothalamus with the pulses causes the patient to eat.

21. A method, as claimed in claim 19, wherein the signal generator generates pulses having a repetition rate of less than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes an increase in satiety for the patient.

22. A method, as claimed in claim 19, wherein the signal generator generates pulses having a repetition rate of greater than 100 Hz and wherein the step of surgically implanting the at least one electrode comprises a step of implanting the stimulation portion in the lateral hypothalamus, wherein electrical stimulation of the lateral hypothalamus with the pulses causes a reduction in appetite for the patient.

23. A method, as claimed in claim 19, wherein the signal generator generates pulses having a repetition rate of greater than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes a reduction in satiety for the patient.

24. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion into the infusion site, wherein the stimulation site and the infusion site are each a respective one of a paraventricular nucleus, a lateral hypothalamus, and a ventral medial hypothalamus of the brain of the patient.

25. A method, as claimed in claim 24, wherein the signal generator generates pulses having a repetition rate of less than 100 Hz and wherein the step of surgically implanting the at least one electrode comprises a step of implanting the stimulation portion in the lateral hypothalamus, wherein electrical stimulation of the lateral hypothalamus with the pulses causes the patient to eat.

26. A method, as claimed in claim 24, wherein the signal generator generates pulses having a repetition rate of less than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes an increase in satiety for the patient.

27. A method, as claimed in claim 24, wherein the signal generator generates pulses having a repetition rate of greater than 100 Hz and wherein the step of surgically implanting the at least one electrode comprises a step of implanting the stimulation portion in the lateral hypothalamus, wherein electrical stimulation of the lateral hypothalamus with the pulses causes a reduction in appetite for the patient.

28. A method, as claimed in claim 24, wherein the signal generator generates pulses having a repetition rate of greater than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes a reduction in satiety for the patient.

29. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion into the infusion site, wherein the at least one drug is one of an antagonist and a blocker substance and wherein the step of surgically implanting the catheter comprises a step of surgically implanting the discharge portion in a paraventricular nucleus of the brain of the patient, wherein drug infusion of the at least one drug into the paraventricular nucleus causes an increase in satiety for the patient.

30. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion into the infusion site, wherein the at least one drug is an agonist and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes an increase in satiety for the patient.

31. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion into the infusion site, wherein the at least one drug is one of an agonist, a blocking substance, and an anesthetic and wherein the step of surgically implanting the catheter comprises a step of surgically implanting the discharge portion in a lateral hypothalamus of the brain of the patient, wherein drug infusion of the at least one drug into the lateral hypothalamus causes a decrease in hunger for the patient.

32. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion into the infusion site, wherein the at least one drug is one of an agonist, an antagonist, and an anesthetic and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes a reduction in satiety for the patient.

33. A method for therapeutically treating an eating disorder of a patient having a central nervous system including a brain and a spinal cord, by at least one of drug infusion into and electrical stimulation of the central nervous system, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient;

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient;

coupling the proximal end of the electrode to the signal generator;

operating the signal generator to stimulate the stimulation site; and operating the pump to discharge a predetermined dosage of at least one drug through the discharge portion of the catheter into the infusion site while the signal generator is stimulating the stimulation site, whereby an eating disorder is treated by at least one of electrical stimulation of the stimulation site and drug infusion into the infusion site, wherein the at least one drug is one of an agonist and an antagonist and wherein the step of surgically implanting the catheter comprises a step of surgically implanting the discharge portion in a lateral hypothalamus of the brain of the patient, wherein drug infusion of the at least one drug into the lateral hypothalamus causes an increase in hunger for the patient.

34. A method for therapeutically treating an eating disorder of a patient having a central nervous system including a brain and a spinal cord, the method comprising the steps of:

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient; and operating the pump to discharge a predetermined dosage of at least one drug through the discharge portion of the catheter into the predetermined infusion site, whereby an eating disorder of the patient is treated by drug infusion of the at least one drug into the infusion site on the central nervous system, wherein the at least one drug is one of an antagonist and a blocker substance and wherein the step of surgically implanting the catheter comprises a step of surgically implanting the discharge portion in a paraventricular nucleus of the brain of the patient, wherein drug infusion of the at least one drug into the paraventricular nucleus causes an increase in satiety for the patient.

35. A method for therapeutically treating an eating disorder of a patient having a central nervous system including a brain and a spinal cord, the method comprising the steps of:

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient; and operating the pump to discharge a predetermined dosage of at least one drug through the discharge portion of the catheter into the predetermined infusion site, whereby an eating disorder of the patient is treated by drug infusion of the at least one drug into the infusion site on the central nervous system, wherein the at least one drug is an agonist and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes an increase in satiety for the patient.

36. A method for therapeutically treating an eating disorder of a patient having a central nervous system including a brain and a spinal cord, the method comprising the steps of:

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient; and operating the pump to discharge a predetermined dosage of at least one drug through the discharge portion of the catheter into the predetermined infusion site, whereby an eating disorder of the patient is treated by drug infusion of the at least one drug into the infusion site on the central nervous system, wherein the at least one drug is one of an agonist, a blocking substance, and an anesthetic and wherein the step of surgically implanting the catheter comprises a step of surgically implanting the discharge portion in a lateral hypothalamus of the brain of the patient, wherein drug infusion of the at least one drug into the lateral hypothalamus causes a decrease in hunger for the patient.

37. A method for therapeutically treating an eating disorder of a patient having a central nervous system including a brain and a spinal cord, the method comprising the steps of:

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient; and operating the pump to discharge a predetermined dosage of at least one drug through the discharge portion of the catheter into the predetermined infusion site, whereby an eating disorder of the patient is treated by drug infusion of the at least one drug into the infusion site on the central nervous system, wherein the at least one drug is one of an agonist, an antagonist, and an anesthetic and wherein the step of surgically implanting the catheter comprises a step of surgically implanting the discharge portion in one of a paraventricular nucleus and a ventral medial hypothalamus of the brain of the patient, wherein drug infusion of the at least one drug into one of the paraventricular nucleus and the ventral medial hypothalamus causes a reduction in satiety for the patient.

38. A method for therapeutically treating an eating disorder of a patient having a central nervous system including a brain and a spinal cord, the method comprising the steps of:

surgically implanting a pump and a catheter having a proximal end coupled to the pump and a discharge portion that lies adjacent a predetermined infusion site in the central nervous system of the patient, the predetermined infusion site being a site on the central nervous system that controls at least one of hunger and satiety for the patient; and operating the pump to discharge a predetermined dosage of at least one drug through the discharge portion of the catheter into the predetermined infusion site, whereby an eating disorder of the patient is treated by drug infusion of the at least one drug into the infusion site on the central nervous system, wherein the at least one drug is an agonist and an antagonist and wherein the step of surgically implanting the catheter comprises a step of surgically implanting the discharge portion in a lateral hypothalamus of the brain of the patient, wherein drug infusion of the at least one drug into the lateral hypothalamus causes an increase in hunger for the patient.

39. A method for therapeutically treating an eating disorder of a patient having a central nervous system including a brain and a spinal cord, the method comprising the steps of:

surgically implanting at least one electrode having a proximal end coupled to a signal generator and having a stimulation portion that lies adjacent a predetermined stimulation site in the central nervous system of the patient, the predetermined stimulation site being a site on the central nervous system that controls at least one of hunger and satiety for the patient; and operating the signal generator to generate a signal to be applied on the electrodes to stimulate the stimulation site, whereby the eating disorder of the patient is treated by electrical stimulation of the predetermined stimulation site with the signal generated by the signal generator, wherein the stimulation site is one of a paraventricular nucleus, a lateral hypothalamus, and a ventral medial hypothalamus of the brain of the patient.

40. A method, as claimed in claim 39, wherein the signal generator generates pulses having a repetition rate of less than 100 Hz and wherein the step of surgically implanting the at least one electrode comprises a step of implanting the stimulation portion in the lateral hypothalamus, wherein electrical stimulation of the lateral hypothalamus with the pulses causes the patient to eat.

41. A method, as claimed in claim 39, wherein the signal generator generates pulses having a repetition rate of less than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes an increase in satiety for the patient.

42. A method, as claimed in claim 39, wherein the signal generator generates pulses having a repetition rate of greater than 100 Hz and wherein the step of surgically implanting the at least one electrode comprises a step of implanting the stimulation portion in the lateral hypothalamus, wherein electrical stimulation of the lateral hypothalamus with the pulses causes a reduction in appetite for the patient.

43. A method, as claimed in claim 39, wherein the signal generator generates pulses having a repetition rate of greater than 100 Hz and wherein the step of surgically implanting the at least one electrode comprises a step of implanting the stimulation portion in one of the ventral medial hypothalamus and the paraventricular nucleus, wherein electrical stimulation of one of the ventral medial hypothalamus and the paraventricular nucleus with the pulses causes a reduction in satiety for the patient.

44. A method for therapeutically treating an eating disorder of a human patient having a central nervous system including a brain and a spinal cord, the method comprising the steps of:

surgically implanting at least one electrode within the central nervous system, the electrode having a proximal end coupled to a signal generator and having a stimulation portion that is implanted at a predetermined stimulation site that is one of a paraventricular nucleus and a lateral hypothalamus of the brain of the patient, the paraventricular nucleus and the lateral hypothalamus controlling at least one of hunger and satiety for the patient; and operating the signal generator to generate a signal to be applied on the electrodes to stimulate the stimulation site, whereby the eating disorder of the patient is treated by electrical stimulation of the predetermined stimulation site with the signal generated by the signal generator.

45. A method, as claimed in claim 44, wherein the signal generator generates pulses having a repetition rate of less than 100 Hz and wherein the step of surgically implanting the at least one electrode comprises a step of implanting the stimulation portion in the lateral hypothalamus, wherein electrical stimulation of the lateral hypothalamus with the pulses causes the patient to eat.

46. A method, as claimed in claim 44, wherein the signal generator generates pulses having a repetition rate of less than 100 Hz and wherein the step of surgically implanting the at least one electrode comprises a step of implanting the stimulation portion in the paraventricular nucleus, wherein electrical stimulation of the paraventricular nucleus with the pulses causes an increase in satiety for the patient.

47. A method, as claimed in claim 44, wherein the signal generator generates pulses having a repetition rate of greater than 100 Hz and wherein the step of surgically implanting the at least one electrode comprises a step of implanting the stimulation portion in the lateral hypothalamus, wherein electrical stimulation of the lateral hypothalamus with the pulses causes a reduction in appetite for the patient.

48. A method, as claimed in claim 44, wherein the signal generator generates pulses having a repetition rate of greater than 100 Hz and wherein the step of surgically implanting the at least one electrode comprises a step of implanting the stimulation portion in the paraventricular nucleus, wherein electrical stimulation of the paraventricular nucleus with the pulses causes a reduction in satiety for the patient.

* * * * *